United States Patent [19]

Drewlow

[11] Patent Number: Plant 6,397

[45] Date of Patent: Nov. 15, 1988

[54] STREPTOCARPUS PLANT NAMED ORION

[75] Inventor: Lyndon W. Drewlow, Ashtabula, Ohio

[73] Assignee: Mikkelsens, Inc., Ashtabula, Ohio

[21] Appl. No.: 9,377

[22] Filed: Jan. 30, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Orion characterized by its numerous pliable short leaves in rosette form, blue violet flower colors, compact growth habit, ease of propagation, floriferous habit, tolerance to low light and high temperature, ability to ship well, and by its long lasting, non-shattering flowers.

1 Drawing Sheet

The present invention relates to a new and distinct cultivar of Streptocarpus plant, botanically known as *Streptocarpus×hybridus,* and known by the cultivar name Orion. Orion was developed by me through controlled breeding by crossing Mikkelsen Seedling 82-1015-30 (seed parent)×Mikkelsen Seedling 82-1069-30 (pollen parent).

Asexual reproduction by me by leaf cuttings has shown that the unique features of this new Streptocarpus are stabilized and are reproduced true to type in successive propagations.

The following characteristics distinguish Orion from both its parent varieties and other cultivated Streptocarpus of this type known and used in the floriculture industry:

1. Orion is characterized with numerous short leaves in a rosette instead of one large leaf that characterizes many older Streptocarpus cultivars such as Apollo. This results in a cluster of flowers in the center of the plant making an attractive 10 cm flowering pot plant. Apollo is an unpatented cultivar as is the cultivar Pluto referred to below.

2. Orion propagates very well from leaf cuttings, producing numerous plantlets in 8 to 10 weeks depending on the time of year. It is also early to flower when compared to older cultivars, with a well rooted plant from a 72 cell pack developing into a flowering plant in six to eight weeks in a 10 cm pot.

3. Orion is similar in plant spread and height to Janus and Ariadne; smaller than Pluto and Ulysses; and larger than Minerva and Pegasus. Janus, Ariadne, Ulyssus, Minerva and Pegasus are disclosed in pending applications.

4. Leaves are smaller in size than Pluto and Ulyssus; similar in size to Janus and Ariadne, and larger than Pegasus.

5. Orion is very floriferous due to the large number of flower stalks produced per leaf axil, and the average of 3 blooms per flower stalk. It is similar in flowering habit to Janus, with Ulyssus having a longer flower stalk and Pegasus a shorter flower stalk.

6. Flower size of Orion is smaller than Pluto and Ulyssus but the number of flowers produced is greater than those two cultivars; smaller than Ariadne but similar in number of flowers; equal in size and number to Janus, and equal in size but more in number than Pegasus.

7. Flower color of Orion is a lighter blue violet than either Pluto or Janus.

8. Orion has leaves that bend well for sleeving as well as long lasting flowers that do not shatter easily, thereby making Orion an excellent shipping cultivar. Janus, Pegasus and Ariadne are also excellent shippers while Pluto does not ship well.

9. Orion has shown the ability to flower both under the lower light conditions of winter (December to February) and under the high temperatures of summer (July to September) without ever going out of bloom under greenhouse conditions.

10 Orion has the ability to tolerate watering with 40° F. water without foliar spotting, and to tolerate fairly high light levels in summer without leaf bronzing.

The accompanying color photograph illustrates in perspective view the overall appearance of Orion, with the colors being as true as it is reasonably possible to obtain in a color reproduction of this type.

The following is a detailed description of my new Streptocarpus cultivar based on plants produced under commercial practices in Greenhouses of Mikkelsens Inc., Ashtabula, Ohio. Color references are made to The Royal Horticultural Society Colour Chart (R.H.S.), except where general colors of ordinary dictionary significance are used.

Classification:

*Botanical.*—*Streptocarpus×hybridus,* cv. Orion.

Parentage: Controlled cross between Mikkelsen seedling 82-1015-30 and Mikkelsen seedling 82-1069-30.

Propagation:

A. *Type cutting.*—Leaf.

B. *Time to develop plantlets.*—Summer: 8 weeks at 20° C.; Winter: 10 weeks at 20° C.

C. *Rooting habit.*—Numerous, fine, fibrous.

Plant description:

A. *Form.*—Leaves are rosette, extending from a crown at the soil line, with flower stalks forming at the leaf midrib. Many leaves in a symmetrical pattern.

B. *Habit of growth.*—Vigorous, very free flowering, never going out of bloom once it starts blooming under greenhouse conditions. Flowers carried above foliage.

C. *Height from soil line.*—15 to 20 cm to top of blooms at maturity.

D. *Spread.*—45 to 55 cm at maturity. Leaf Size: 20 to 25 cm in length and 6 to 8 cm in width at the widest point; leaf size can vary greatly with cultural conditions. Quantity: Mature plant may have more than 20 leaves. Leaf Shape: Elliptical. Texture: Lower surface rugose with veins protruding and pubescent; upper surface rugose and pubescent. Margin: Finely crenate. Color: Young foliage top side 146A; under side 148C. Mature foliage top side 137B; under side 146D. Ribs and veins: Pinnate. Rib and vein color: 146D. Leaf tips: Obtuse. Leaf base: Acute.

Flower description: Flowers open one at a time on the individual flower stalks.

A. *Fully expanded.*—40 to 45 mm.

B. *Stem.*—Single, reddish purple in color, long, slightly pubescent and round; several from a leaf midrib.

C. *Form.*—Funnel shaped in an umbel with upper two petals reflexed and lower petals flattened to give an overall flat appearance.

D. *Flower bud description.*—20 to 25 mm at maturity, tubular with the end larger diameter than the rest; 5 green calyx folded over the basal end.

E. *Flowers borne.*—In clusters of 2 to 4 flowers per flower stalk, with 3 the most common, carried above foliage. Pedicels of the flowers in the inflorescence vary in length.

F. *Quantity of flowers.*—Mature plant can have more than 20 flower stalks open with up to 4 flowers each.

G. *Permanence.*—Long lasting, 10 days or longer.

Color:

A. *Tonality from a distance.*—Light blue, throat creamy white with purple streaking extending into the lower 3 petals.

B. *Upper surface of petals.*—85A violet streaked with 90A.

C. *Under surface of petals.*—91B.

D. *Throat.*—4D.

E. *Discoloration.*—Slight fading of old flowers.

Petals:

A. *Texture.*—Satin.

B. *Appearance.*—Individually lobed with slight crenate margins, top 2 petals reflexed and smaller than the 3 bottom petals which are flat.

C. *Arrangement.*—Regularly united into an almost circular shape.

D. *Persistence.*—10 days or longer, remain on plant in dry form until picked.

E. *Fragrance.*—None.

Reproductive organs:

A. *Stamens.*—2 fertile; 2 sterile, very small. Anther shape: 2 fertile; interconnected and flat. Anther color: Purple. Filament: Attached to petals for 2 mm and 2 sterile free standing for 1 mm, fertile for 6 mm. Pollen color: White.

B. *Pistils.*—Stigma shape: 2 lobed, flattened, rounded at end of lobes. Stigma color: White with purple cast. Stigma size: 2 mm across. Style color: White. Style size: 5 mm. Ovaries: Numerous, 12–14 mm on receptive pistil, purplish.

Disease resistance: No disease problems to date.

Other important characteristics: Compact growth habit combined with highly floriferous nature makes Orion suitable for 10 cm pot plant production on a year round basis. Orion is further enhanced by its long lasting, non-shattering flowers and pliable small leaves that do not scorch under high light or spot with cold water.

I claim:

1. A new and distinct cultivar of Streptocarpus plant named Orion, as illustrated and described, and particularly characterized by its numerous pliable short leaves in rosette form, blue violet flower colors, compact growth habit, ease of propagation, floriferous habit, tolerance to low light and high temperature, ability to ship well, and by its long lasting, non-shattering flowers.

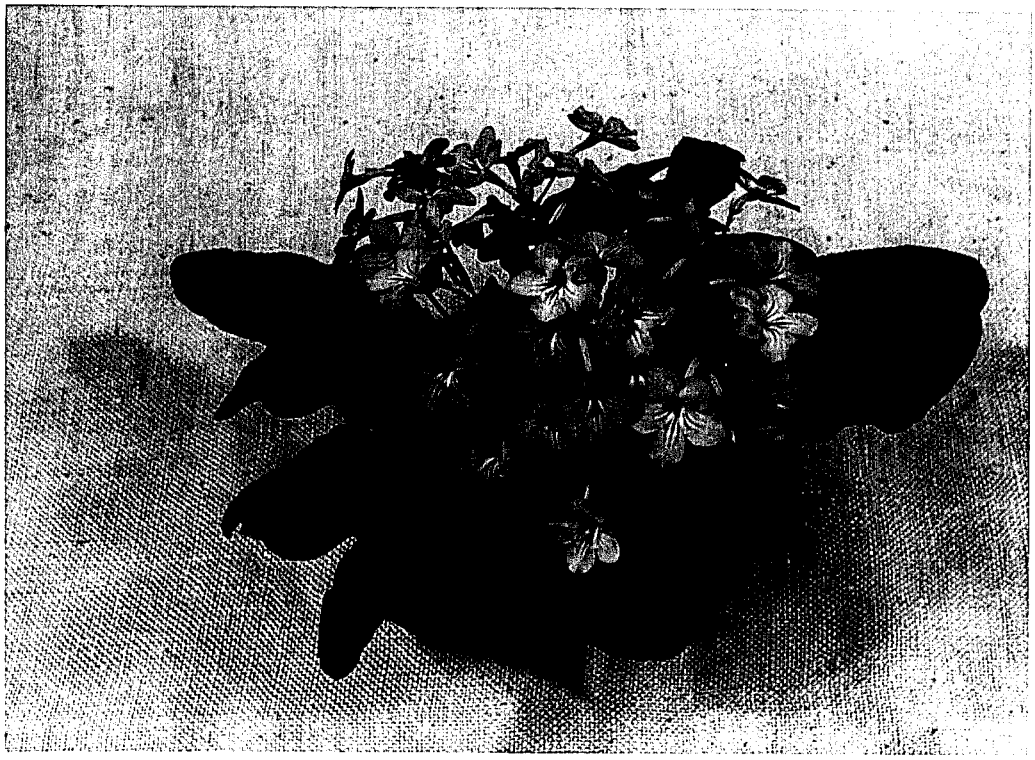

* * * * *